(12) United States Patent
Bruder

(10) Patent No.: US 7,505,552 B2
(45) Date of Patent: Mar. 17, 2009

(54) METHOD FOR RECORDING CARDIO X-RAY CT PICTURES, AND CARDIO CT SYSTEM

(75) Inventor: Herbert Bruder, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/790,761

(22) Filed: Apr. 27, 2007

(65) Prior Publication Data
US 2007/0253526 A1 Nov. 1, 2007

(30) Foreign Application Priority Data
Apr. 28, 2006 (DE) ........................ 10 2006 019 919

(51) Int. Cl.
*G01N 23/00* (2006.01)
(52) U.S. Cl. ............................. 378/8; 378/20
(58) Field of Classification Search .............. 378/4, 378/8–9, 15, 13, 14, 16, 19, 20
See application file for complete search history.

(56) References Cited

U.S. PATENT DOCUMENTS 6,763,082 B2 7/2004 Ozaki
6,819,738 B2 * 11/2004 Hoffman ..................... 378/19
2005/0089133 A1 * 4/2005 Tsuyuki ......................... 378/8

\* cited by examiner

*Primary Examiner*—Hoon Song
(74) *Attorney, Agent, or Firm*—Harness, Dickey & Pierce, P.L.C.

(57) ABSTRACT

A method for scanning a beating heart with the aid of a spiral CT system and a cardio CT system are disclosed. In at least one embodiment, rhythm signals of the beating heart are recorded and stored in a temporally correlated fashion, and only detector data that originate from a selected cycle area of the cardiac cycle are measured in order to reconstruct the tomographic section image data or volume data, the scanning being carried out with a runup distance and a runout distance for the purpose of complete scanning of the subarea of the patient with the beating heart on the basis of the spiral scanning. According to at least one embodiment of the invention, at least one of the requisite runup distance and runout distance is determined on the basis of the measured cycles of the current rhythm signal of the patient, and an appropriate program code is present in the cardio CT system.

11 Claims, 3 Drawing Sheets

METHOD FOR RECORDING CARDIO X-RAY CT PICTURES, AND CARDIO CT SYSTEM

PRIORITY STATEMENT

The present application hereby claims priority under 35 U.S.C. §119 on German patent application number DE 10 2006 019 919.7 filed Apr. 28, 2006, the entire contents of which is hereby incorporated herein by reference.

FIELD

Embodiments of the invention generally relate to a method for scanning a beating heart with the aid of a spiral CT system. For example, they may relate to one wherein at least one focus of a focus detector system having a multirow detector is moved around a patient with a feed, and in which case an X-ray beam emanating from the at least one focus scans at least a subarea of the patient having an extent in a system axis direction and including a beating heart located there, the intensity of the beams and their spatial orientation data being measured as detector output data and stored. Moreover, rhythm signals of the beating heart are recorded and stored in a temporally correlated fashion. Furthermore, only detector data that originate from a selected cycle area of the cardiac cycle are measured or used in order to reconstruct the tomographic section image data or volume data, the scanning being carried out with a runup distance and a runout distance for the purpose of complete scanning of the subarea of the patient with the beating heart on the basis of the spiral scanning.

BACKGROUND

It is generally known that in the course of preparing cardio CT pictures with the aid of multirow detectors that are moved spirally around a patient a table feed is set such that each desired slice position can be reconstructed in a scanning area, selected by the user, relating to each heart phase. The temporal reference between the measured value projections and the heartbeat of the patient is generally determined in this case by an ECG or another rhythm signal of the beating heart. The reconstruction of a first or last image slice in this case requires a certain runup distance of the spiral or, correspondingly, a certain runout distance of the spiral. To date, this runup distance or runout distance of the scanning has been selected to be constant independently of the heart rate of the patient. An unnecessarily high dose burden can thereby come about for the patient.

SUMMARY

In at least one embodiment, the invention is directed to a method for scanning a beating heart with the aid of a spiral CT which reduces or even minimizes, as far as possible, the dose burden for the patient. Furthermore, in at least one embodiment, specify a corresponding spiral CT system is specified for carrying out such a method.

The inventor has realized in at least one embodiment that, with an increasing number of rows of the detectors used for preparing cardio CT pictures, owing to the practice of assuming a constant maximum cardiac cycle, and with the constant runup distance resulting therefrom, there is an unnecessarily increased dose burden for the patient during spiral scanning that likewise rises in relation to overall scanning of the heart with an increasing number of rows.

It is therefore proposed, in at least one embodiment, to match the length of the runup distance or runout distance for scanning the heart region of the patient adaptively to the current heart rate of this patient.

If, for example, the dose saving ε is calculated with the aid of the following formula on the basis of the standard values for the runup distance that are currently generally adopted, this results in a 20% reduction in the patient dose when use is made of an adaptively matched runup distance and runout distance during scanning:

$$\varepsilon = \frac{2 \cdot (T_{fix} - T_{cycle})}{2 \cdot T_{fix} + \frac{\Delta z}{z_{rot}} \cdot T_{rot}},$$

wherein it holds that:
$\Delta z$=size of the heart volume to be imaged, 140 mm
$z_{rot}$=feed in z-direction, 11.5 mm
$T_{cycle}$=current cardiac cycle duration of the patient, 800 ms, corresponding to 75 beats/per minute
$T_{fix}$=permanently adopted cycle time of the heart in accordance with the prior art, corresponding to 1500 ms.

In accordance with this basic idea, in at least one embodiment the inventor proposes both an optimized method for scanning a beating heart with the aid of a spiral CT system, and a cardio CT system, which lead to a reduced dose burden for the patient according to this optimized runup distance or runout distance.

Consequently, a method for scanning a beating heart with the aid of a spiral CT system that has at least the following features:

- at least one focus of a focus detector system having a multirow detector is moved spirally around a patient with a feed $z_{rot}$, wherein
- an X-ray beam emanating from the at least one focus scans at least a subarea of the patient having an extent in a system axis direction of $\Delta z$ and including the beating heart located there, the intensity of the beams and their spatial orientation data being measured as detector output data and stored,
- rhythm signals of the beating heart are recorded and possibly stored in a temporally correlated fashion, and
- only detector data that originate from a selected cycle area of the cardiac cycle are measured or used in order to reconstruct the tomographic section image data or volume data,
- the scanning being carried out with a runup distance and a runout distance for the purpose of complete scanning of the subarea $\Delta z$ of the patient with the beating heart on the basis of the spiral scanning, is optimized to the effect that the runup distance and/or runout distance required for complete scanning of the subarea $\Delta z$ are determined on the basis of the measured cycles of the current rhythm signal of the patient.

It is possible here to determine the runup distance and runout distance from the following equation:

$$z_{pre} = z_{post} = \left(\frac{T_{cycle}}{T_{rot}} + \frac{1}{4 \cdot m}\right) \cdot z_{rot} - \frac{N_S \cdot S}{2},$$

the following variables being used:
m=number of focus detector systems;

$N_s$=number of detector rows;
S=collimated slice thickness per detector row;
$T_{cycle}$=measured cycle duration of the current rhythm signal;
$T_{rot}$=rotation time of the focus for one revolution;
$z_{pre}$=runup distance;
$z_{post}$=runout distance;
$z_{rot}$=feed per revolution of the focus.

In order to execute this system, it is possible to use a focus detector system having one or a number of, preferably two, focus detector systems, it being advantageous, in turn, when use is made of two focus detector systems if the latter are arranged offset by 90° from one another on a gantry.

The cardiac rhythm signal can be, for example, an ECG signal, or it is also possible to use another signal correlated with the heartbeat, for example a pressure signal of the patient's mechanical pulse.

There is further proposed, in at least one embodiment, a cardio CT system that has:
- at least one focus detector system having a multirow detector that is moved spirally around a patient with a feed $z_{rot}$,
  wherein an X-ray beam emanating from the at least one focus scans at least a subarea of the patient having an extent in a system axis direction of $\Delta z$ and including a beating heart located there, the intensity of the beams and their spatial orientation data being measured as detector output data and stored in a data memory,
- a means for detecting rhythm signals of the beating heart, the detected rhythm signals being stored in a temporally correlated fashion, and
- an arithmetic logic unit having stored computer programs for controlling the cardio CT system and for reconstructing tomographic section image data or volume data from the measured detector data from a selected cycle area of the cardiac cycle.

According to at least one embodiment of the invention, it is proposed for the purpose of improving this cardio CT system that there is present in the arithmetic logic unit of this cardio CT system a program code that is executed in operation and controls the beginning and end of scanning in a spatial and temporal fashion, the scanning being carried out, for the purpose of complete scanning of the subarea of the patient, with a runup distance and a runout distance that are calculated on the basis of the measured cycles of the current rhythm signal of the patient.

In accordance with the previously described method and its particular designs, the arithmetic logic unit can also contain and execute in operation program code that executes this previously described method in whole or part.

BRIEF DESCRIPTION OF THE DRAWINGS

The invention is described in more detail below with reference to example embodiments and with the aid of the figures, only the features required to understand the invention being illustrated. The following reference symbols are used here: 1: cardio CT system; 2: first X-ray tube; 3: first detector; 4: second X-ray tube; 5: second detector; 6: gantry housing; 7: patient; 8: patient couch; 9: system axis/z-axis; 10: control and arithmetic logic unit; 11: memory of the control and arithmetic logic unit; 12: control and data line between gantry and control and arithmetic logic unit; 13: ECG line; 14: focus; 15: beam; 16: heart; 17: spiral track; $\Delta z$: subarea of the patient with beating heart; m: number of focus detector systems; $N_S$=number of detector rows; $Prg_x$: computer programs; S=collimated slice thickness per detector row; $T_{cycle}$=measured cycle duration of the current ECG; $T_{rot}$=rotation time of the focus for one revolution; x, y, z: Cartesian coordinates; $z_{pre}$: adaptive runup distance; $z_{post}$: adaptive runout distance; $z'_{pre}$: fixed runup distance; $z'_{post}$: fixed runout distance; $z_{rot}$: feed per revolution of the focus; $\phi$: fan angle; $\kappa$: cone angle.

In detail.

DETAILED DESCRIPTION OF THE EXAMPLE EMBODIMENTS

Figure 1:
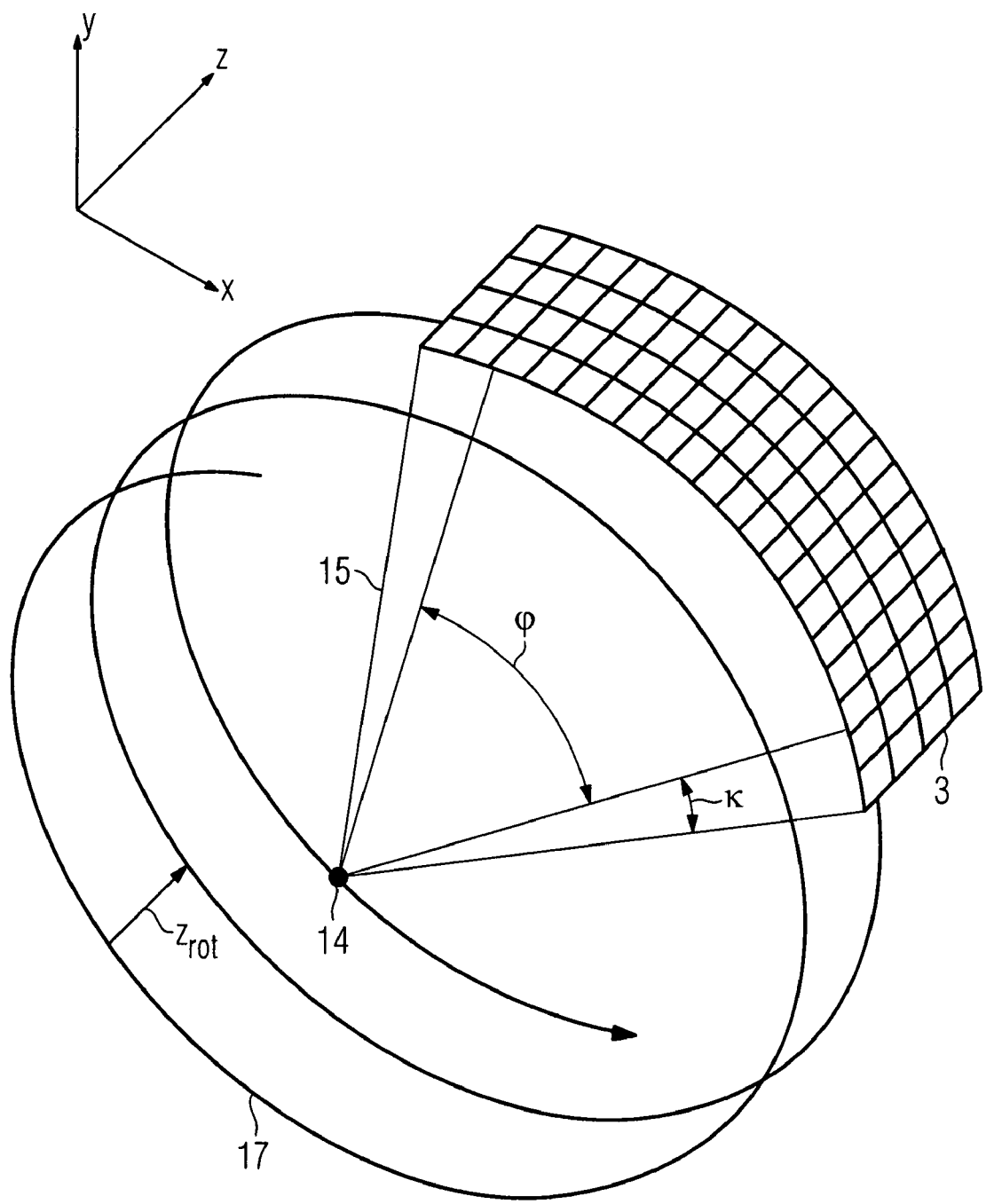
FIG. 1 shows a schematic of a spiral scan with a multirow detector.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

In order to improve understanding of an example embodiment of the invention, FIG. 1 shows a three-dimensional schematic of the spiral path 17 of a focus detector system having a focus 14 and an opposite detector 3. Emanating from the focus 14, a beam 15 with a fan angle $\phi$ and a cone angle $\kappa$ in the z-direction is directed onto an opposite multirow detector 3, having four rows here. The feed $z_{rot}$ set here corresponds to the spacing on the spiral tracks 17 in a z-direction. With this type of scanning, regions in which the scanning beams do not achieve complete projection are produced at the beginning and at the end of the spiral track.

Figure 2:
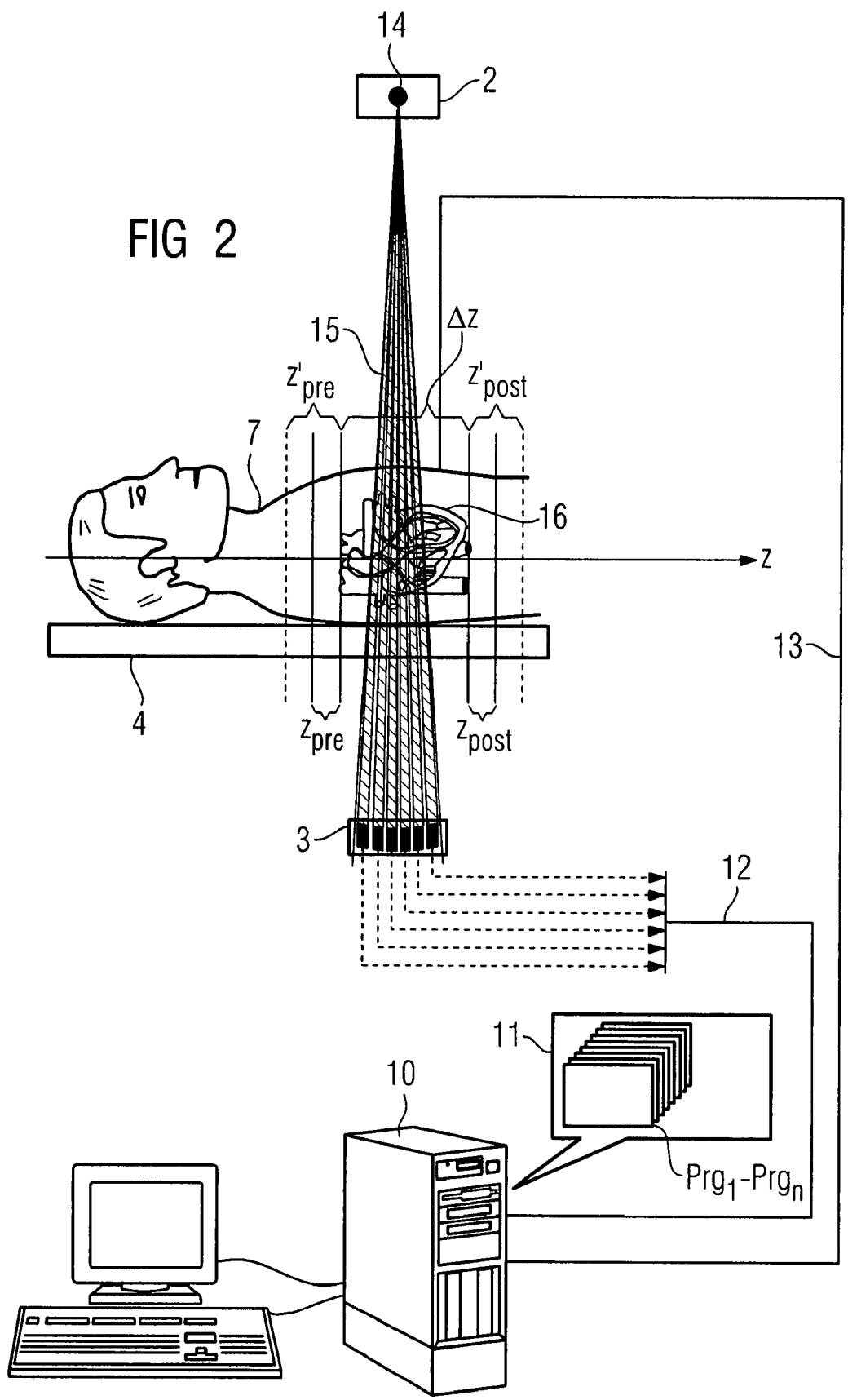
FIG. 2 shows a longitudinal section through a patient whose heart is being scanned by a focus detector system of a CT.

FIG. 2 shows such a situation with a longitudinal section through a patient 7, a focus detector system being illustrated that is equipped with the beam 15 that emanates from an X-ray tube 2 with a focus 14 and is directed onto an opposite detector 3 with six detector rows illustrated. The patient 7 is located on a movable couch 8 that is displaced in a z-direction 9 during a circular revolution of X-ray tube 2 and detector 3 such that a spiral run of the scan takes place relative to the patient 7. The detector output data of the detector 3 are led via data lines 12 to a control and arithmetic logic unit 10, where the measured projections and the reconstruction of tomographic pictures therefrom are calculated. In addition, via an ECG system likewise integrated in the control and arithmetic logic unit 10, the patient 7 detects electrical rhythm signals, ECG signals, via an ECG line 13, and thus records the instantaneous movement or rest phase of the heart 16. A reconstruction of tomographic pictures of the heart can be obtained in a known way from the sum of these data, use generally being made to this end exclusively of data that originate from rest phases. The computer programs $Prg_1$ to $Prg_n$ required to this end are contained in a memory 11 of the control and arithmetic logic unit 10.

It is to be pointed out here that these data can, of course, also be stored on simple data carriers or other storage media, and can be loaded in an appropriate computing system as required.

As may be seen from the sectional illustration of FIG. 2, the subarea $\Delta z$ of the patient 7 in which the beating heart 16 is located and in which the tomographic pictures or volume data are to be reconstructed extends from the beginning up to the end of the heart in the z-direction. As previously stated, it is not possible to begin scanning the heart exactly at these boundaries of the subarea $\Delta z$ of the scan, but it is necessary to take account of an additional runup distance so that a complete set of projections is recorded in the subarea $\Delta z$ for all slice planes in each case, there also being the additional complication that the heart moves during this time, that is to say complete projections from the rest data and from the cycle phases of the heart that are considered must be available.

Use has been made to this end in the prior art of a previously determined fixed runup distance $z'_{pre}$ and of a previously determined fixed runout distance time $z'_{post}$ which ensure that complete projections of the cycle phases of the heart that are being considered are present in the subarea $\Delta z$. When fixing these runup and runout distances, a relatively long cycle duration of the heart was used for reasons of safety.

In accordance with the above-described idea of an example embodiment of the invention, instead of the fixed runup and runout distances $z'_{pre}$ and $z'_{post}$ use is made of a runup distance $z_{pre}$ adapted to the actual heart rate, and of a corresponding adapted runout distance $z_{post}$, which can lead to a significant dose reduction for the entire examination.

Figure 3:
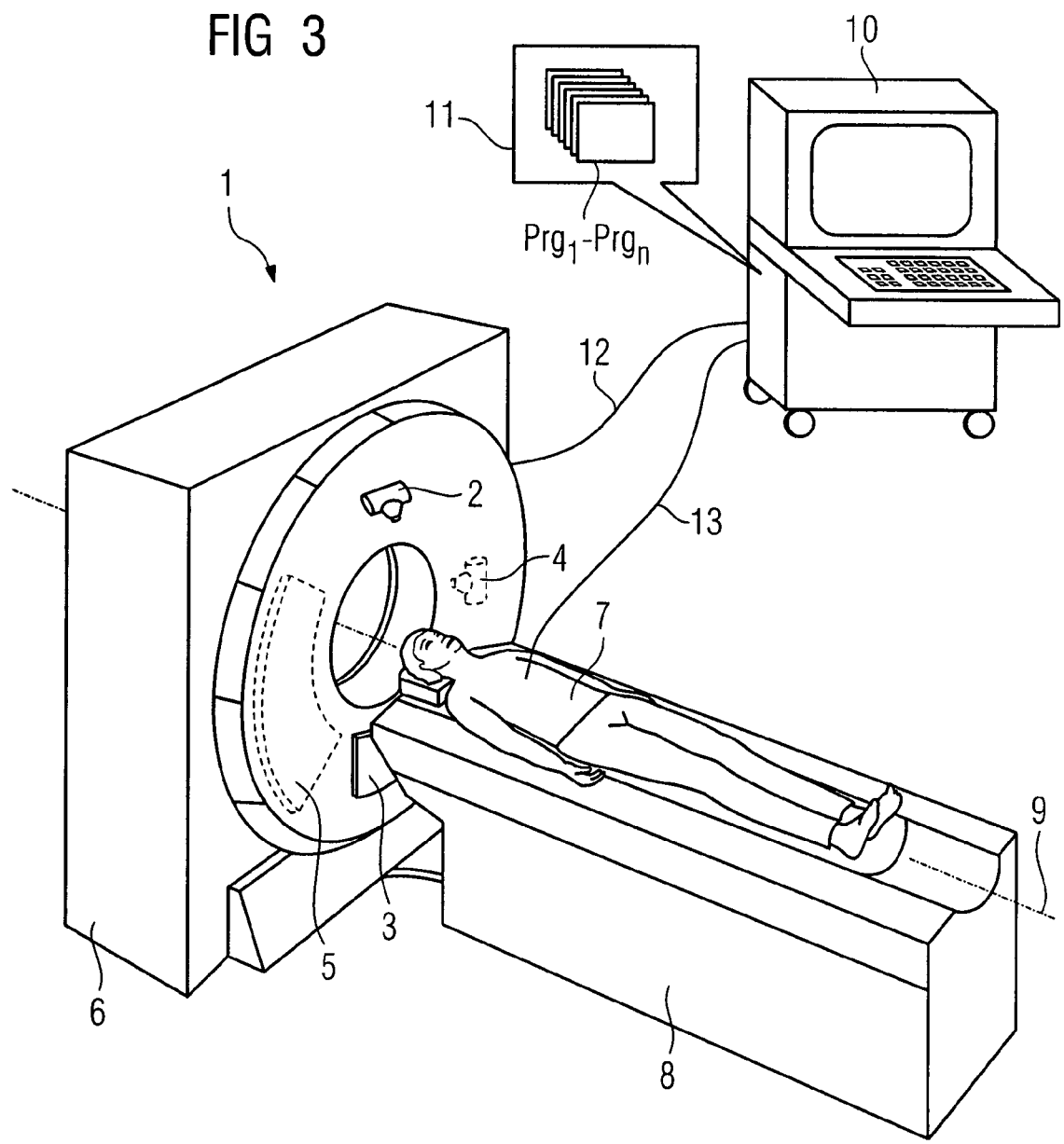
FIG. 3 shows a 3D illustration of a cardio CT system according to an embodiment of the invention.

FIG. 3 shows, once again, a complete cardio CT system 1 having a gantry housing 6 in which there are arranged at least one X-ray tube 2 with an opposite detector 3 on a revolving gantry (not illustrated here). The patient 7 lies on a patient couch 8 that can be displaced along the system axis 9. A spiral scan is produced around the patient 7 by the cooperation between the circularly revolving gantry with the X-ray tube 2 and the detector 3, and the longitudinal displacement of said patient. The control and arithmetic logic unit 10 with the programs $Prg_1$ to $Prg_n$ located in the memory 11 controls the gantry via a control and data line 12 via which the detector output data can also be transmitted back again to the control and arithmetic logic unit 10. In addition, the control and arithmetic logic unit 10 includes an ECG system that derives rhythm signals from the beating heart of the patient 7 via an ECG line 13, and therefore determines the current cycle phase of the heart.

According to an example embodiment of the invention, the control and arithmetic logic unit 10 can also calculate the requisite, if minimal runup distance of the patient at the beginning and end of the scan, use being made to this end of current data of the patient 7 with reference to his heart rate.

It is possible as an option to arrange on the gantry additional focus/detector units that are preferably positioned in a fashion offset by 90° from the first focus/detector unit. Present in the illustration shown here are an additional X-ray tube 4 (illustrated with dashes) and an opposite detector 5 having an offset of 90° from the first X-ray tube 2 or from the first detector 3. It is possible by using a number of such tubes/detector units to improve the time resolution of the scan substantially. As a rule, the patient 7 is additionally injected with contrast agent for a cardio CT examination, although this has not been explicitly depicted in the illustration shown here, because it is not essential to an example embodiment of the invention. Such administrations of contrast agent can likewise be performed in principle by the control and arithmetic logic unit 10 with the aid of appropriate computer programs and a dosing device.

It goes without saying that the abovementioned features of an example embodiment of the invention can be used not only in the respectively specified combination, but also in other combinations or on their own, without departing from the scope of the invention.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scanning a beating heart with the aid of a spiral CT system, the method comprising:

spirally moving at least one focus of a focus detector system, including a multirow detector, around a patient with a feed;

recording rhythm signals of the beating heart and storing the recorded signals in a temporally correlated fashion;

determining at least one of a runup distance and runout distance required for complete scanning of a subarea based on measured cycles of a current rhythm signal of the patient;

scanning, via an X-ray beam emanating from the at least one focus, at least the subarea of the patient including an extent in a system axis direction and including the beating heart located there, an intensity of the beams and their spatial orientation data being measured as detector output data and stored, the scanning being carried out with the runup distance and the runout distance for complete scanning of the subarea of the patient with the beating heart on the basis of the spiral scanning; and reconstructing at least one of the tomographic section image data and volume data based only on detector data that originate from a selected cycle area of the cardiac cycle; wherein the runup distance and runout distance are determined from the following equation:

$$z_{pre} = z_{post} = \left(\frac{T_{cycle}}{T_{rot}} + \frac{1}{4 \cdot m}\right) \cdot z_{rot} - \frac{N_S \cdot S}{2},$$

where
m=number of focus detector systems;
$N_s$=number of detector rows;
S=collimated slice thickness per detector row;
$T_{cycle}$=measured cycle duration of the current rhythm signal;
$T_{rot}$=rotation time of the focus for one revolution;
$z_{pre}$=runup distance;
$z_{post}$=runout distance;
$z_{rot}$=feed per revolution of the focus.

2. The method as claimed in claim 1, wherein exactly one focus detector system is used.

3. The method as claimed in claim 1, wherein exactly two focus detector systems are used.

4. The method as claimed in claim 3, wherein the two focus detector systems are arranged offset by 90° from one another on a gantry.

5. The method as claimed in claim 1, wherein an ECG signal is used as rhythm signal.

6. The method as claimed in claim 1, wherein a pressure signal of the patient's mechanical pulse is used as rhythm signal.

7. A cardio CT system, comprising:
at least one focus detector system including a multirow detector that is movable spirally around a patient with a feed, an X-ray beam emanating from the at least one focus being usable to scan at least a subarea of the patient including an extent in a system axis direction and including a beating heart located there, the intensity of the beams and their spatial orientation data being measurable as detector output data and storable in a data memory;

means for detecting rhythm signals of the beating heart, the detected rhythm signals being stored in a temporally correlated fashion; and an arithmetic logic unit including stored computer programs with program code for controlling the cardio CT system and for reconstructing tomographic section image data or volume data from the measured detector data from a selected cycle area of the cardiac cycle, a program code executable in operation that, when executed, is usable to,
control, in a spatial and temporal fashion, the beginning and end of complete scanning of the subarea of the patient, and
calculate a runup distance and a runout distance based on the measured cycles of the current rhythm signal of the patient, the runup distance and runout distance being calculated from the following equation:

$$z_{pre} = z_{post} = \left(\frac{T_{cycle}}{T_{rot}} + \frac{1}{4 \cdot m}\right) \cdot z_{rot} - \frac{N_S \cdot S}{2},$$

where
m=number of focus detector systems;
$N_s$=number of detector rows;
S=collimated slice thickness per detector row;
$T_{cycle}$=measured cycle duration of the current rhythm signal;
$T_{rot}$=rotation time of the focus for one revolution;
$z_{pre}$=runup distance;
$z_{post}$=runout distance;
$z_{rot}$=feed per revolution of the focus.

8. A cardio CT system, comprising:
means for detecting rhythm signals of a beating heart, the detected rhythm signals being stored in a temporally correlated fashion;

means for determining at least one of a runup distance and runout distance required for complete scanning of a subarea based on measured cycles of a current rhythm signal of the patient;

at least one focus detector system including a multirow detector that is movable spirally around the patient with a feed, an X-ray beam emanating from the at least one focus being usable to scan at least the subarea of the patient including an extent in a system axis direction and including the beating heart located there, the intensity of the beams and their spatial orientation data being measurable as detector output data and storable in a data memory; and means for reconstructing at least one of the tomographic section image data and volume data based on only detector data that originate from a selected cycle area of the cardiac cycle; wherein the runup distance and runout distance are calculated from the following equation:

$$z_{pre} = z_{post} = \left(\frac{T_{cycle}}{T_{rot}} + \frac{1}{4 \cdot m}\right) \cdot z_{rot} - \frac{N_S \cdot S}{2},$$

where
m=number of focus detector systems;
$N_s$=number of detector rows;
S=collimated slice thickness per detector row;
$T_{cycle}$=measured cycle duration of the current rhythm signal;
$T_{rot}$=rotation time of the focus for one revolution;
$z_{pre}$=runup distance;
$z_{post}$=runout distance;
$z_{rot}$=feed per revolution of the focus.

9. The method as claimed in claim 8, wherein exactly one focus detector system is used.

10. The method as claimed in claim 8, wherein exactly two focus detector systems are used.

11. The method as claimed in claim 8, wherein an ECG signal is used as rhythm signal.

* * * * *